(12) United States Patent
Shapland et al.

(10) Patent No.: US 12,377,243 B1
(45) Date of Patent: Aug. 5, 2025

(54) INTERMITTENT INTRAVESICAL THERAPEUTIC ADMINISTRATION SYSTEM

(71) Applicant: UroPharma Ltd., Norfolk (GB)

(72) Inventors: Howard Shapland, Woodton (GB); Scott Glickman, Kingswood (GB); Gabriel Korn, Norwich (GB)

(73) Assignee: UroPharma Limited, Norfolk (GB)

( * ) Notice: Subject to any disclaimer, the term of this patent is extended or adjusted under 35 U.S.C. 154(b) by 0 days.

(21) Appl. No.: 18/903,887

(22) Filed: Oct. 1, 2024

(51) Int. Cl.
*A61M 25/00* (2006.01)

(52) U.S. Cl.
CPC .... *A61M 25/0017* (2013.01); *A61M 25/0097* (2013.01)

(58) Field of Classification Search
CPC ............ A61M 25/002; A61M 25/0017; A61M 25/0097; A61M 25/0111; A61M 2025/0062; A61M 2025/0681; A61M 2210/1085; A61M 2210/1089; A61M 27/008; A61M 25/01; A61M 25/04; A61M 2210/1078; A61M 25/0113; A61M 2025/0175; A61M 25/00; A61M 2202/0496
See application file for complete search history.

(56) References Cited

U.S. PATENT DOCUMENTS

| | | |
|---|---|---|
| 3,331,371 A | 7/1967 | Rocchi et al. |
| 3,394,705 A | 7/1968 | Abramson |

(Continued)

FOREIGN PATENT DOCUMENTS

| | | |
|---|---|---|
| CN | 1145260 A | 3/1997 |
| DE | 10112630 A1 | 7/2002 |

(Continued)

OTHER PUBLICATIONS

International Searching Authority—International Search Report, pertaining to International Application No. PCT/GB2012/052617 dated Jan. 21, 2013, together with the Written Opinion of the International Searching Authority, 10 pages.

(Continued)

*Primary Examiner* — Adam Marcetich
(74) *Attorney, Agent, or Firm* — Sunstein LLP

(57) ABSTRACT

An intravesical intermittent instillation catheter includes a tube containing a urinary lumen and an instillation lumen. The proximal end has a set of drainage eyelets, formed in a wall of the tube, that are in communication with the urinary lumen as well as a set of instillation eyelets, formed at a tip of the proximal end, in communication with the instillation lumen. A sheath is slidably mounted to surround the tube and having first and second axial positions wherein, in the first position, the drainage eyelets are exposed and, in the second position, the drainage eyelets are covered by the proximal end of the sheath. In operation of the catheter, when the sheath is in the first position, drainage of urine can proceed through a path including the drainage eyelets, the urinary lumen, a drainage connector, and a urinary collection bag and, when the sheath is in the second position, instillation of the medicament can thereafter proceed from a syringe, through an instillation connector, the instillation lumen, and the instillation eyelets and into the bladder.

7 Claims, 10 Drawing Sheets

(56) References Cited

U.S. PATENT DOCUMENTS

| | | | |
|---|---|---|---|
| 3,894,540 A * | 7/1975 | Bonner, Jr. | A61M 25/0111 |
| | | | 604/171 |
| 3,981,299 A | 9/1976 | Murray | |
| 4,150,673 A | 4/1979 | Watt | |
| 4,227,533 A | 10/1980 | Godfrey | |
| 4,834,702 A | 5/1989 | Rocco | |
| 5,085,636 A | 2/1992 | Burns | |
| 5,112,306 A | 5/1992 | Burton et al. | |
| 5,792,118 A | 8/1998 | Kurth et al. | |
| 5,971,972 A | 10/1999 | Rosenbaum | |
| 6,093,191 A | 7/2000 | Porter | |
| 6,132,364 A | 10/2000 | Rottenberg et al. | |
| 6,270,053 B1 | 8/2001 | Eshel | |
| 8,007,488 B2 | 8/2011 | Ravenscroft | |
| 8,038,644 B2 | 10/2011 | Glickman | |
| 10,188,827 B2 | 1/2019 | Glickman et al. | |
| 2005/0038413 A1 | 2/2005 | Sansoucy | |
| 2005/0124969 A1 | 6/2005 | Fitzgerald et al. | |
| 2006/0173419 A1 | 8/2006 | Malcolm | |
| 2006/0184224 A1 | 8/2006 | Angel | |
| 2006/0195059 A1 | 8/2006 | Freyman et al. | |
| 2007/0213671 A1 | 9/2007 | Hiatt | |
| 2007/0232981 A1 | 10/2007 | Ravencroft | |
| 2008/0091166 A1 | 4/2008 | Fitzgerald et al. | |
| 2008/0228258 A1 | 9/2008 | Gendts et al. | |
| 2008/0287888 A1 | 11/2008 | Ravenscroft | |
| 2008/0312578 A1 | 12/2008 | DeFonzo | |
| 2009/0240234 A1 | 9/2009 | Doerr | |
| 2009/0264860 A1 | 10/2009 | Hiatt | |
| 2010/0204771 A1 | 8/2010 | Olson | |
| 2012/0053564 A1 | 3/2012 | Ravenscroft | |
| 2012/0168324 A1 | 7/2012 | Carleo | |
| 2012/0179144 A1 * | 7/2012 | Carleo | A61M 25/0017 |
| | | | 604/544 |
| 2012/0239006 A1 | 9/2012 | Wijay et al. | |
| 2014/0163530 A1 * | 6/2014 | Frenkel | A61M 27/00 |
| | | | 604/540 |
| 2015/0290421 A1 * | 10/2015 | Glickman | A61M 25/003 |
| | | | 604/30 |
| 2019/0143078 A1 * | 5/2019 | Tierney | A61M 25/0017 |
| | | | 604/544 |
| 2020/0187918 A1 * | 6/2020 | Wiygul | A61M 25/0017 |
| 2021/0077775 A1 * | 3/2021 | Vogt | A61M 39/24 |
| 2021/0299410 A1 * | 9/2021 | Wiesman | A61M 25/0017 |
| 2022/0040449 A1 * | 2/2022 | Sremcevic | A61M 25/007 |
| 2022/0280746 A1 * | 9/2022 | Wiesman | A61M 25/0084 |
| 2024/0252784 A1 * | 8/2024 | Martins | A61M 25/002 |

FOREIGN PATENT DOCUMENTS

| | | |
|---|---|---|
| EP | 0245211 | 11/1987 |
| GB | 1534219 A | 11/1978 |
| GB | 2448892 A | 11/2008 |
| GB | 2484598 A | 4/2014 |
| JP | H09253215 A | 9/1997 |
| JP | 2001137350 | 5/2001 |
| WO | 199951293 A1 | 10/1999 |
| WO | 2002/28465 A1 | 4/2002 |
| WO | 2007/079152 A1 | 7/2007 |
| WO | 2008/097949 A1 | 8/2008 |
| WO | 2008/132431 A1 | 11/2008 |
| WO | 2010/014569 A1 | 2/2010 |
| WO | 2011/019359 A1 | 2/2011 |
| WO | 2011/014201 A1 | 3/2011 |
| WO | 2011/045790 A1 | 4/2011 |
| WO | 2013/057517 A1 | 4/2013 |

OTHER PUBLICATIONS

International Searching Authority—International Preliminary Report on Patentability, pertaining to International Application No. PCT/GB2008/001253 dated Jul. 24, 2008, together with the Written Opinion of the International Searching Authority, 9 pages.

Great Britain Application Serial No. GB0708427.0, United Kingdom Search Report mailed Jul. 25, 2007, 3 pages.

* cited by examiner

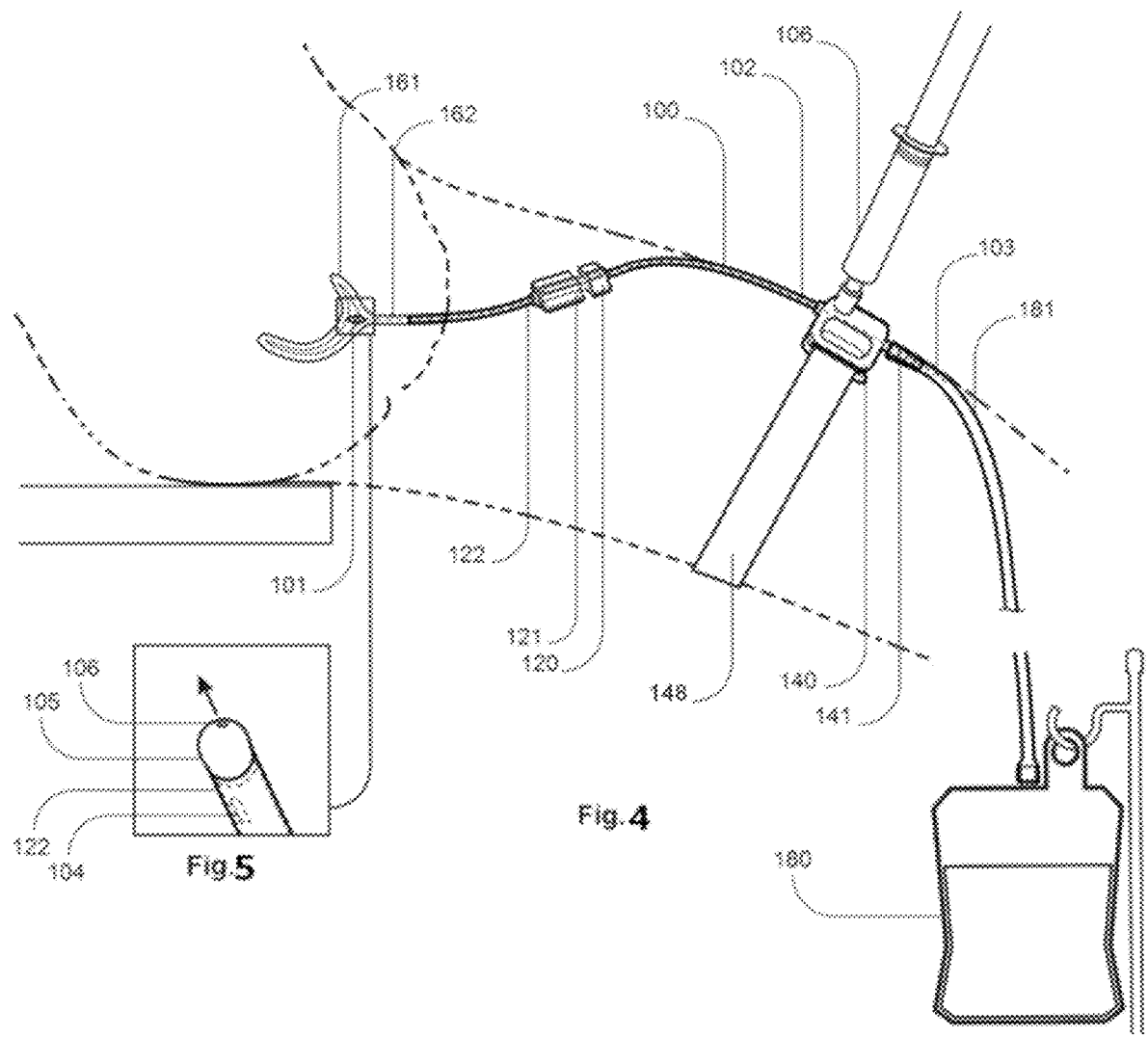

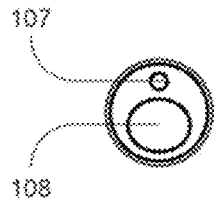
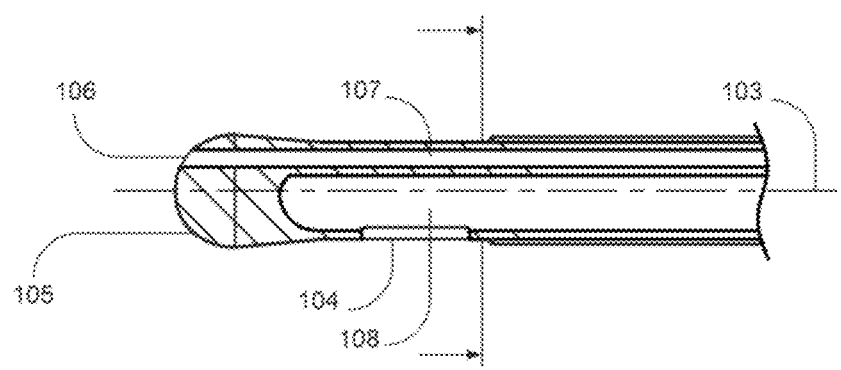
Fig.10
Fig.9
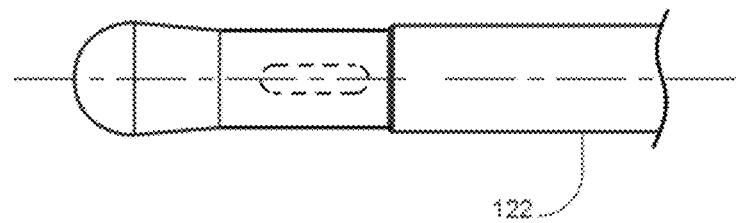
Fig.8

INTERMITTENT INTRAVESICAL THERAPEUTIC ADMINISTRATION SYSTEM

TECHNICAL FIELD

The present invention relates to urinary catheters for direct-to-target instillation of medicine, into an empty urinary bladder cavity typically immediately after previous urine drainage, with a view to incorporating both a urinary drainage requirement and a medicament instillation capability in a safe, accurate and precise procedure.

BACKGROUND ART

There are several conditions and micturition anomalies involving the bladder, such as urinary tract infection, overactive bladder syndrome, incontinence, and urinary tract inflammation and cancers, that the preferred delivery of therapeutic agents is directly into the bladder's urinary compartment to directly treat the bladder inner lining tissue known as urothelium.

Owing to the bladder's unique anatomical characteristics, which provide resistances to absorption of some chemicals from its urinary cavity into and through its urothelium that can otherwise predispose to their uptake into the systemic circulation, the conditions that cause pathological damage to bladder urothelium cannot be reliably, safely and effectively treated with orally administered drugs or injections into the systemic compartment of the body. Direct-to-bladder local drug administration via a catheter for therapeutic targeting of tissue is more rational and efficient than systemic treatments via oral administration, trans-tissue absorption or injection, and may reduce side effects compared to treatments that course through the systemic circulation before delivery into the bladder's urinary compartment. Pharmacotherapy through direct-to-bladder administration is called intravesical instillation, vesical instillation, intravesical treatment, intravesical therapy, intravesicular or intravesical administration.

With intravesical therapy, the therapeutic agent is delivered in a liquid phase through a catheter that is inserted into the bladder through the urethra or a fistula tracking between skin and the bladder's urinary cavity. In this manner, the therapeutic agent can affect the cells that cover the bladder interior minimizing side effect risks in other parts of the body.

A fundamental principle of good therapeutics treatment is to maximize a treatment's benefits while minimizing its drug burden. To achieve a high level of efficacy and to maximize this therapeutic effect with minimum drug burden, it is initially necessary to drain any amount of urine accumulated in the bladder to minimize dilution of the therapeutic agent within the urinary compartment and in contact with the intended target, as well as to prevent loss of the therapeutic agent by post-instillation urination or drainage through catheter-assisted urine voiding. When loss of the therapeutic agent by urination before the drug produces its desired effects, can be avoided, it is feasible to achieve the administration of a predetermined dosage of the therapeutic agent. Depending on the disease or condition being investigated or treated, intravesical therapy may require a single instillation of a single drug, multiple instillations of a single drug, multiple drug instillations as mixtures administered in a single treatment or consecutively administered multiple instillations.

For intravesical therapy, in the medical product marketplace there is a paucity of licensed products specifically configured for this purpose. Generally urinary drainage catheters are designed exclusively for draining urine from the bladder and currently are licensed by regulatory authorities only for that purpose and not for intravesical instillation of a therapeutic agent. Irrigation catheters flush fluids in and out of a hollow organ's cavity rather than deposit medications for treatment. Sometimes urinary drainage catheters are used in an unlicensed context for therapeutic instillation procedures, typically flushing back urine residue, following initial fluid drainage but left in the drainage lumen, back into the bladder in a manner creating risks of infection. Because unlicensed procedures generally are unacceptable to be performed by nurses, but only by doctors who are obligated to take full responsibility for their actions (which as just described may involve infection risks) and healthcare providers typically are unwilling to offer unlicensed treatments for patients to self-administer, therefore intravesical therapy is uncommon, and especially so, outside specialist medical facilities.

Dosing accuracy and minimizing of residual drug in the drainage lumen is critical for any drug delivery device or drug delivery system dispensing an active substance, for patient safety and reliability of dosing from treatment to treatment. Regulatory authorities require pharmaceutical preparations, such as liquids, tablets, and capsules, to be produced with known dosages within narrow parameters. Accordingly, every treatment's unit dose in a manufactured and packaged batch is within a narrow dosing tolerance, for example within 2% of the declared dosage. Urine drainage catheters are not designed for ensuring such dosing accuracy because of varying lengths of drainage lumen from manufacture to manufacture, causing a great variation in residual fluid left in the catheter after instillation. This is also not desirable from a safety perspective, particularly when using toxic anti-cancer therapy drugs. Furthermore, fluid normally flows from the bladder though the drainage lumen to drain the bladder of urine, typically into a drainage bag. After the instillation process, drug instilled into the bladder, and some residual drug in the drainage lumen, likely will flow away from the bladder and so be wasted, thus rendering reliably accurate dosing difficult to effect in standard drainage catheters. Drainage catheters typically have no features for prevention of that normal direction of fluid flow.

SUMMARY OF EMBODIMENTS

In accordance with one embodiment, the invention provides an intravesical intermittent instillation catheter. In this embodiment, the catheter includes:
  a tube, dimensioned and shaped for partial insertion into a urinary conduit of a patient, the tube containing a urinary lumen and an instillation lumen, the tube having a distal end and a proximal end, wherein the proximal end has a set of drainage eyelets, formed in a wall thereof, that are in communication with the urinary lumen as well as a set of instillation eyelets, formed at a tip of the proximal end, in communication with the instillation lumen;
  a sheath having a distal end and a proximal end, the sheath being slidably mounted to surround the tube and having first and second axial positions in relation to the tube, wherein, in the first position, the drainage eyelets are exposed and, in the second position, the drainage eyelets are covered by the proximal end of the sheath;
  a valve actuator configured at a distal end of the sleeve, the actuator including (i) a slider coupled to the sheath and sliding with the sheath and (ii) an anchor coupled to the tube, each of the slider and the anchor being configured to be grasped by a different hand, the wherein movement of the slider away from the anchor causes the sleeve to move to the second position so as to cover the eyelets and prevent further flow of urine therethrough; and a hub mechanically coupled to a distal end of the tube and including an instillation connector coupled to the instillation lumen and a drainage connector coupled to the urinary lumen, wherein the drainage connector is configured to be connected to tubing to run to a urinary collection bag and the instillation connector is configured to be coupled to a syringe filled with a medicament for instillation into the bladder.

In operation of the catheter, when the sheath is in the first position, drainage of urine can proceed through a path including the drainage eyelets, the urinary lumen, the drainage connector, and the urinary collection bag and, when the sheath is in the second position, instillation of the medicament can thereafter proceed from the syringe, through the instillation connector, the instillation lumen, and the instillation eyelet and into the bladder.

In a related embodiment, the instillation connector is configured to receive a custom-shaped medicament-containing syringe that is incompatible with a conventional Luer syringe, so as to reduce a risk of inadvertent use of an improper medicament or dosage. In another related embodiment, the valve actuator further includes a one-way latch configured, when the slider has been advanced in the proximal direction, to occupy space between the slider and the anchor so as to prevent return motion of the slider to the distal position for reuse of the catheter.

In another related embodiment, the hub includes a hub insert, to which the tube is attached and configured so that the urinary lumen therein has a flow path to the drainage connector for drainage of urine therethrough and the instillation lumen has a flow path through a hole near the distal end of an external wall of the catheter to receive medicament from a syringe placed in the instillation connector, wherein the hub insert is customized to one size of a specific set of sizes associated with the tube, the instillation lumen, and the urinary lumen, so that the hub can accommodate a variety of sizes associated with the tube, the instillation lumen, and the urinary lumen.

In a further related embodiment, the hub insert includes an integrated check valve, in the flow path between the instillation connector and the hole near the distal end of the external wall of the catheter, to prevent backflow of the medicament during instillation of the medicament. Alternatively or in addition, at its proximal end the sheath has an edge that is generally bevelled to minimize trauma to surrounding tissue when the sheath is moved to the second position. Also, alternatively or in addition, the sheath, over a majority of its length, has an internal diameter that exceeds an external diameter of the catheter, by an amount sufficient to facilitate ready sliding of the sheath over the catheter, but wherein the internal diameter of the sheath is tapered to a tight tolerance near the proximal end of the sheath, with the tolerance still permitting sliding of the sheath while also preventing flow of fluid between the sheath and the exterior of the catheter.

BRIEF DESCRIPTION OF THE DRAWINGS

The preceding features of embodiments will be more readily understood by reference to the following detailed figures, referencing the accompanying drawings, in which:

FIG. 4 is a view of the novel catheter device of FIG. 1 in a second position with the drainage eyelet closed FIG. 5 is ready for medicament instillation, with a syringe connector and a medication syringe, located at an inlet point on the superior face of the access port.

FIG. 5 is a detailed view of the proximal end of the embodiment of FIG. 1 in its second position for medicament instillation.

FIG. 8 is a detailed top view of the distal end of the novel catheter device of FIG. 1 on its initial draining position.

FIG. 9 is a detailed axial section of the top view of the novel catheter device of FIG. 1 in its initial draining position.

FIG. 10 is a detailed cross-section of the tube of the embodiment of FIG. 1 showing the micro-lumen medicament delivery channel in the wall of the tubing and the urine drainage lumen.

DETAILED DESCRIPTION OF SPECIFIC EMBODIMENTS

Definitions. As used in this description and the accompanying claims, the following terms shall have the meanings indicated, unless the context otherwise requires:

A "set" includes at least one member.

The term "patient" refers to a human or animal subject.

The terms "proximal" and "distal" applied to a catheter refer to positions of the catheter relative to the body of a patient. When a catheter device in accordance with an embodiment of the present invention is inserted into a patient, the "proximal" end of the catheter is the portion of the catheter located closest to the body of the patient (for example within the urinary bladder cavity of the patient), and the "distal" end of the catheter is the portion of the catheter more distant from the body of the patient.

The "urethra" is a thin, fibromuscular tube that begins at the lower opening of the bladder and extends through the pelvic and urogenital diaphragms to the outside of the body, called the external urethral orifice.

The urinary catheter is classified by gauge referred to as French, FR or CH. The French size of a catheter is determined by a simple multiplication of 3 (diameters in millimetres multiplied by 3=the French size). For example, if a catheter has a diameter of 4.7 millimetres, then the French (Fr) size is 14. The most commonly utilized indwelling transurethral and suprapubic catheters range from 14 Fr to 16 Fr in both adult females and males. A 14 Fr or 16 Fr is also the standard catheter in most commercially available IUC insertion kits or trays. The full range of sizes is 8 FR to 26 FR in increments of 2.

In the accompanying figures, reference numbers indicate the like elements to make more comprehensible the operational explanation of the present novel catheter device.

Figure 1:
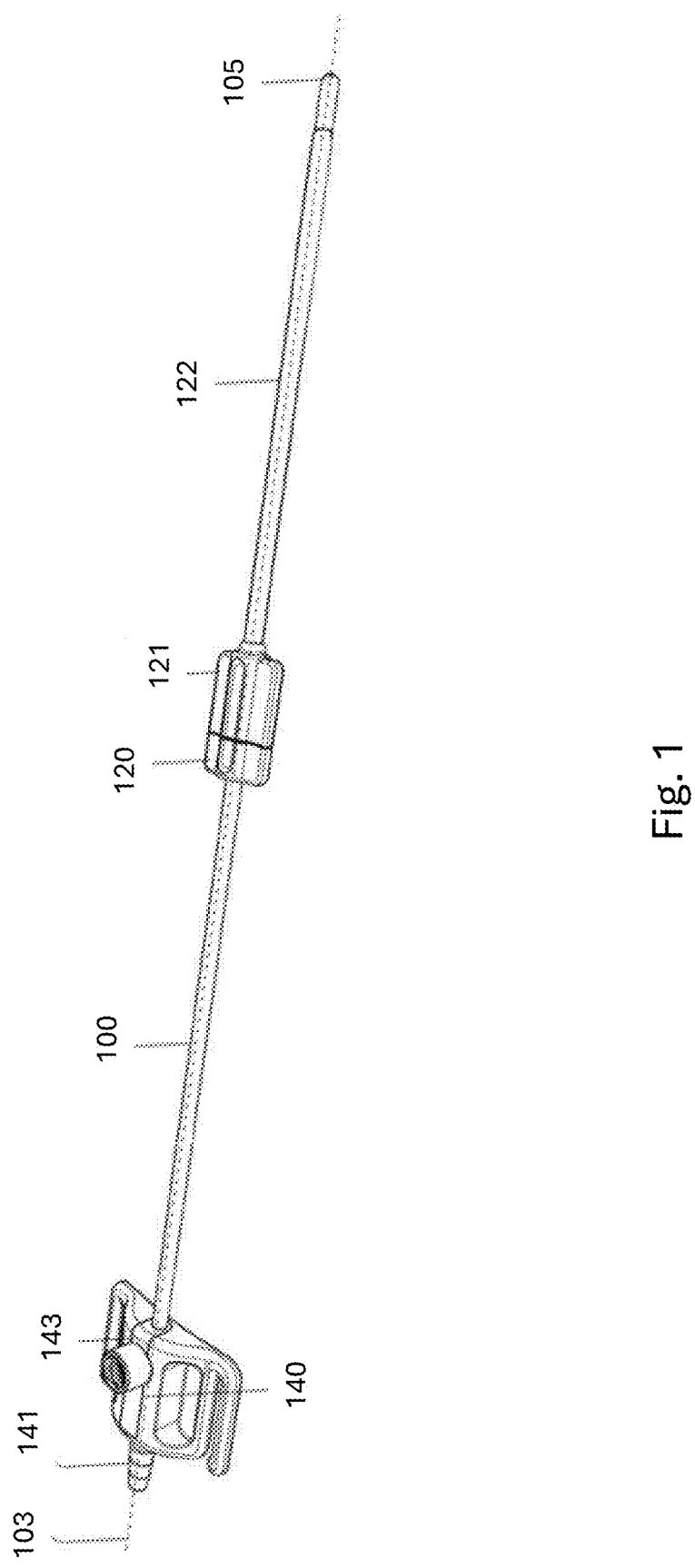
FIG. 1 is a superior perspective view of the medical device ("single-use sterile intravesical intermittent therapeutic medicament instillation catheter") in accordance with an embodiment of the present invention.

FIG. 1 is a superior perspective view of a catheter device in accordance with an embodiment of the present invention. As described in further detail in connection with FIGS. 9 and 10, the catheter embodiment of FIGS. 1, 2, 9, and 10 (among other figures) includes both an instillation lumen through which a medicament can be instilled into the bladder and a urine drainage lumen through which urine can be drained from the bladder. We provide further detail below on how both of these lumens are utilized for instillation of the medicament and drainage of the urine. The embodiment is dimensioned and shaped for partial insertion into the urethra orifice of a patient to access the urinary bladder cavity. As shown in FIG. 1, the tube 100 of the catheter embodiment includes an axially sliding sheath 122 surrounding the catheter 100. The catheter has a tip 105 configured for insertion into the urethra orifice of the subject. This embodiment includes a valve actuator having two sections, each section configured to be grasped by a different hand, including a slider 121 affixed to the sliding sheath 122 and an anchor 120 affixed to the catheter. In the valve actuator, the slider 121 can be moved axially, relative to the anchor 120, between a first position in which the slider 121 is in contact with the anchor 120 and a second position in which slider 121 is spaced apart from one the anchor 120. The motion of the slider 121 causes corresponding motion of the sliding sheath.

Also, as shown in FIG. 1, the distal end of the distal portion of the catheter 100 is coupled to universal hub 140, which has a customized female fitting 143 for a non-Luer syringe for purposes of instillation of a medicament. In turn, the female fitting 143 is coupled to the instillation lumen 107 shown in FIGS. 9 and 10. The universal hub 140 also has a male fitting 141, coupled to the urinary lumen 108 of FIGS. 9 and 10, to receive urinary flow from the bladder. The male fitting 141 has a plurality of axially disposed ridges for securing by friction fit a flexible tubing (identified as item 181 of FIGS. 2 and 4), placed over the ridges, so that urinary flow through the urinary lumen 108 passes through the male fitting 141 and then the flexible tubing 181 to the collection bag 180 of FIGS. 2 and 4.

Figures 2, 3:
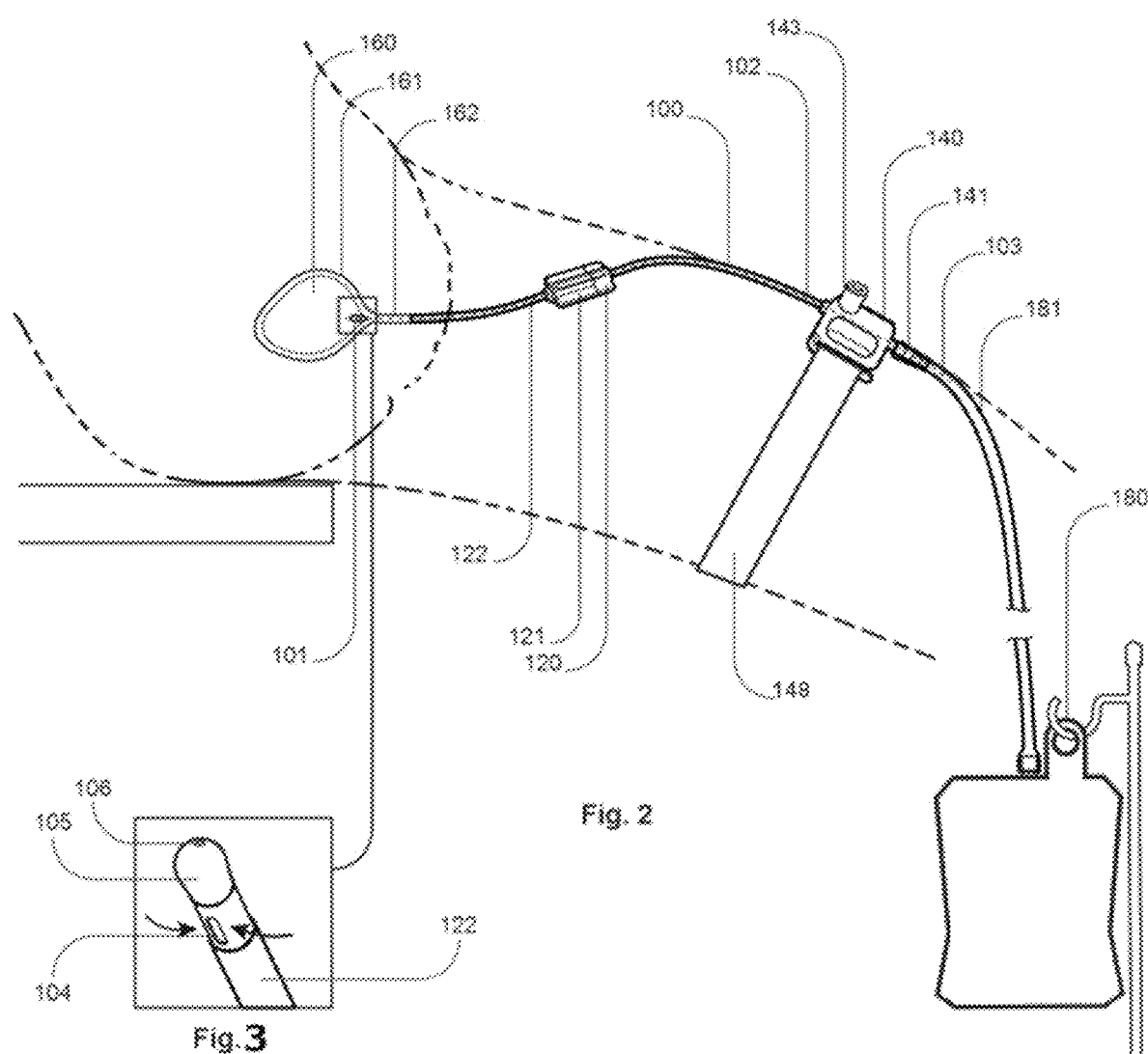
FIG. 2 is a functionality view of an embodiment of the catheter of FIG. 1 wherein the catheter is in an initial draining position, with its distal end inserted into a full bladder of a patient via the urethra, extending outside of the patient to where the catheter tube 100 is connected to the universal hub 140 having male fitting 141 to which is connected to the urine collection bag 180. The universal hub 140 is secuted by strap 148 to the leg of the patient.
FIG. 3 is a detailed view of the distal end of the novel catheter device of FIG. 1 in its initial draining position with the drainage eyelets open FIG. 3.
Figure 6:
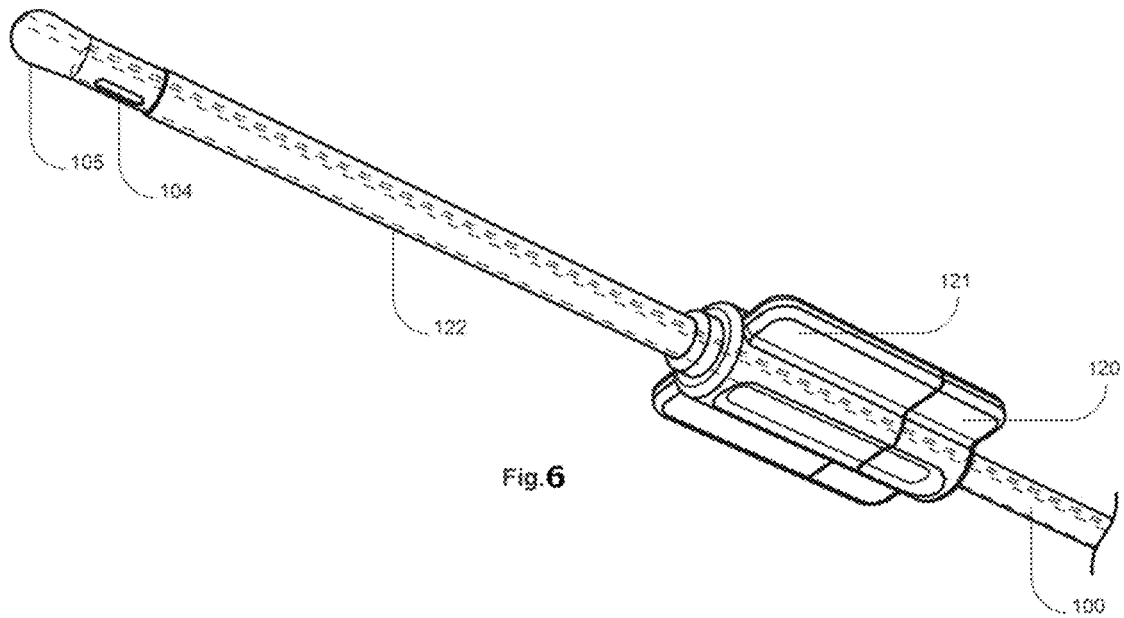
FIG. 6 is a detailed view of the eyelet closure system (distal drainage closing mechanism) of the embodiment of FIG. 1 the drainage is in the open position when supplied (ready for use)

FIGS. 2 and 3 provide views of the embodiment of the device of FIG. 1 in an initial draining configuration, with its proximal end inserted into the bladder of a patient, extending outside of the body and coupled to flexible tubing 181 that empties into urine collection bag 180. In the initial draining position, the slider 121 of the valve actuator is in contact with the anchor 120, and the sliding sheath 122 leaves exposed the set of drainage eyelets 104 shown in FIG. 3. In the initial draining configuration, the device empties the bladder 161 of urine accumulated over time in the bladder cavity 160. Elimination of the urine accumulated from the kidneys prevents dilution of medicament that is later administered, so that the device can thereafter be used to instill an accurate predetermined dosage of a medicament. In the draining configuration, as discussed, the urinary flow is through the drainage eyelets 104, which provide a port to the urinary lumen 108 of FIGS. 9 and 10 contained within the catheter, and then through the urinary lumen 108, then through the universal hub 140 to the male fitting 141, then the tubing 181 and finally the collection bag 180.

In operation of the embodiment 100 shown in FIG. 2, the catheter proximal end 105 is inserted into the urethral orifice to access the bladder cavity 106 to drain urine via the drainage eyelets 104, which initially are placed in the open position with sheath 122 withdrawn from the drainage eyelets 104 when the slider 121 of the valve actuator is in contact with the anchor 120. Urinary flow is down the urinary lumen 108 into the urine collection bag 180. When the urine ceases to flow from the bladder into the bag 180, the eyelets 104 are closed by axially sliding the slider 121 in the proximal direction into a locked position in which the drainage eyelets 104 are covered by sheath 122. The sheath 122 is generally bevelled at the edge of its proximal end to minimize trauma to surrounding tissue that might otherwise be caused by sliding of the sheath to the axially forward position when the drainage eyelets are covered. Additionally, the sheath, over a majority of its length, has an internal diameter that exceeds the external diameter of the catheter, by an amount sufficient to facilitate ready sliding of the sheath over the catheter. Finally, the internal diameter of the sheath is tapered to a tight tolerance near the proximal end of the sheath, with the tolerance still permitting sliding of the sheath while also preventing flow of fluid between the sheath and the exterior of the catheter, FIGS. 4 and 5 correspond to FIGS. 2 and 3 respectively, but now show the catheter embodiment with the sheath 122 moved axially in a proximate direction along the catheter 100 so as to occupy the second position. In the second position, the sheath 122 covers the drain eyelets 104, to prevent fluid flow from the bladder into the urinary lumen. At this point, the bladder 161 has been drained of urine, so that it is now efficacious to cause instillation of medicament into the bladder. In the locked position, the catheter embodiment 100 is configured as a single-use instillation device, because once the sheath 122 is covering the eyelets 104, it cannot be retracted to again expose the eyelets so to prevent a second use of the device, thus avoiding any cross-contamination risks and potential loss of medicament.

Figure 7:
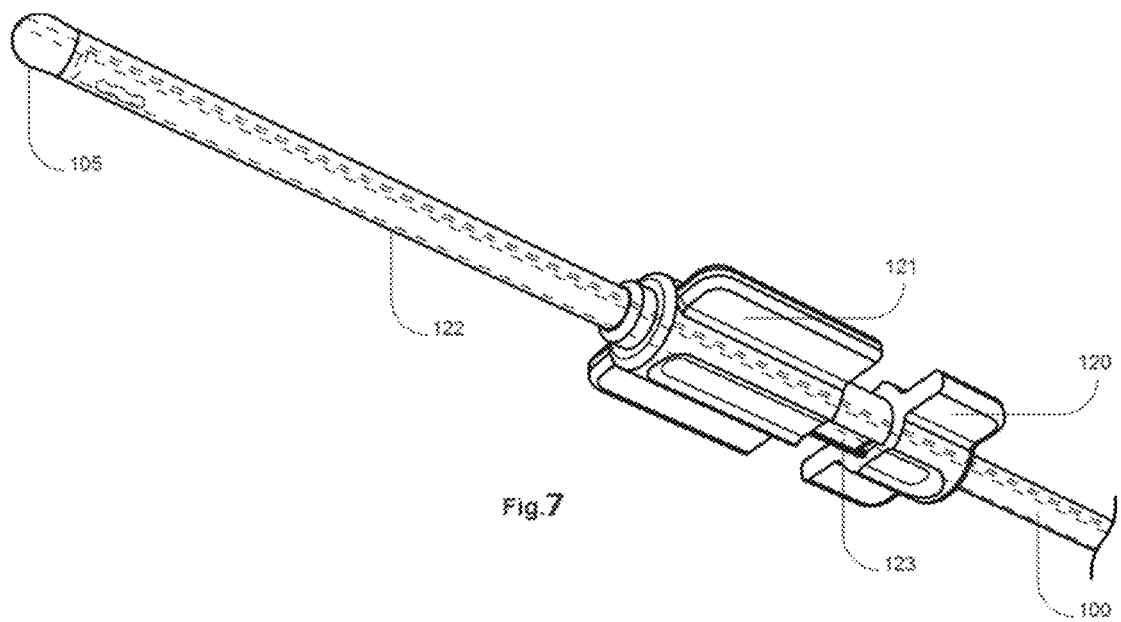
FIG. 7 is a detailed view of the eyelet closure system (distal drainage closing mechanism) of the embodiment of FIG. 1 the drainage is in the closed position after slide activation when the slide mechanism is manually pushed into its forward position.

FIG. 7 is a detailed view of the slider valve system with the slider 121 and sheath 122 disposed in the axially forward (proximal) position to occlude the eyelets 122, so that the catheter embodiment is ready for instillation of medicament. The slider 121 is prevented from being moved distally by virtue of the one-way latch 123, which is configured, when the slider 121 has been advanced in the proximal direction, to occupy space between the slider 121 and the anchor 120 and prevent return motion of the slider to the distal position for reuse of the catheter.

FIG. 8 is a detailed top view of the proximal end of the catheter embodiment in its initial draining position.

FIGS. 9 and 10 provide additional views of the catheter embodiment 100 of FIG. 1. The two lumens run parallel to each other in the catheter 100. FIG. 9 is a detailed vertical-section of the side view of the catheter embodiment of FIG. 1 in its initial draining position, and FIG. 10 is a cross-section of the catheter embodiment of FIG. 1. In its interior, as shown in FIG. 10, the catheter 100 contains two lumens: a urinary lumen 108 and a medicament instillation lumen 107, the latter being typically implemented as a mini-channel of about 0.5 mm diameter in the catheter wall. The urinary lumen 108 is of larger dimensions, allowing substantial urine flow for efficient drainage. It is preferred that the lumen has drainage eyelets 104 at a side of the proximal end for better flow and patient comfort. The instillation lumen 107 presents its medicament outlet orifice 106 at the tip of the catheter 100 at the proximal end 105. As discussed, flow through the urinary lumen 108 originates in the bladder, and runs through the eyelets 104, at the proximal end of the catheter, through the distal portion of the catheter, and then through the universal hub 140 to the male fitting 145, then the tubing 181 and finally the collection bag 180. The instillation lumen 106 parallels the urinary lumen 107 in the catheter embodiment 100 and handles flow of medicament (in a direction opposite that of the draining urinary flow) from a prefilled syringe 106 (in FIGS. 4 and 13) that engages with the female fitting 143 of the universal hub 140, which, in turn, is coupled to the instillation lumen 107 of catheter 100. From the instillation lumen 107, the flow of medicament is through the medicament instillation orifice located in the moulded tip 105 on the proximal portion of the catheter. The medicament is instilled through a female connector 143 located on the universal hub 140, which allows for the coupling of a non-Luer syringe connector 143 designed specifically for medicament instillation into the urinary system, so as to reduce the risk of improper medicament instillation via a standard Luer syringe. The catheter tube 100 is made of a flexible polymeric material and is sealed on its proximal end with an integrated formed soft tip 105 and a medicament delivery orifice 106, incorporated in the moulding process, that are coupled to the instillation lumen.

Figure 11:
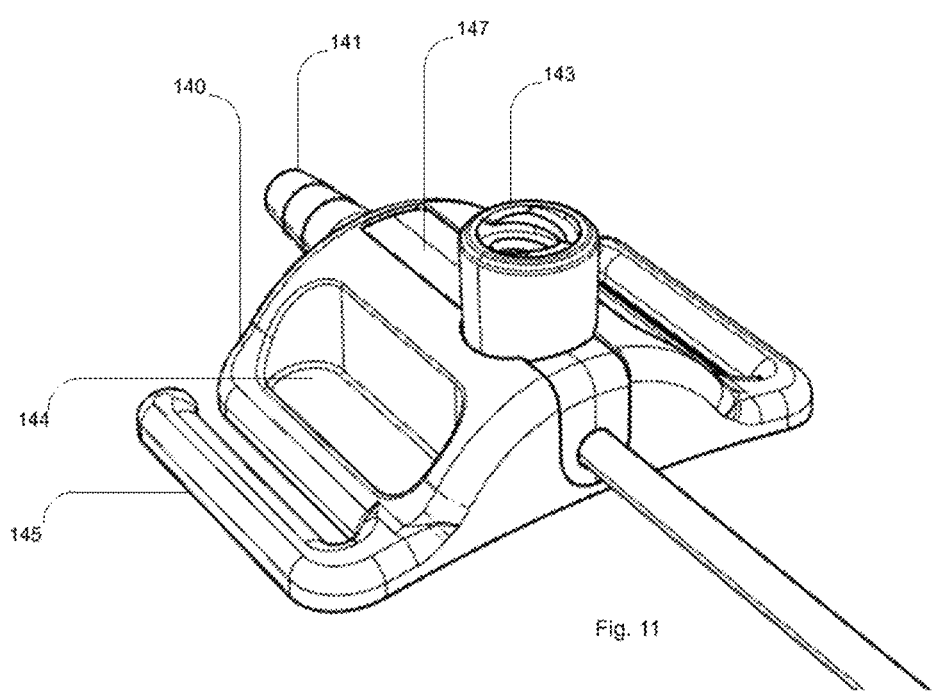
FIG. 11 is a perspective view of the syringe access port 143 and check-valve (one-way non-return) 149 seated in the universal hub of the embodiment of FIG. 1
Figure 12:
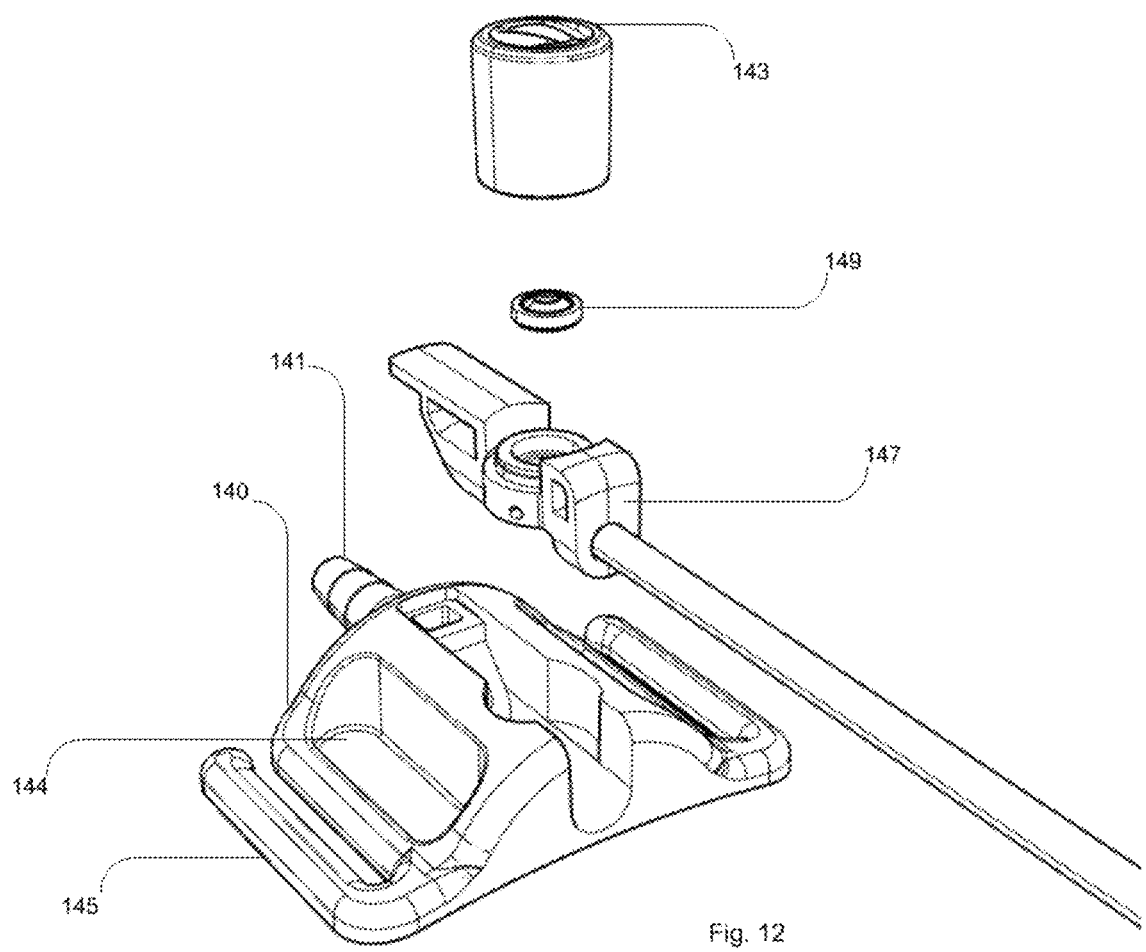
FIG. 12 is an exploded view of the embodiment of FIG. 1 showing universal hub 140 and components including the female syringe access port 143 located in the hub insert 147, the leg strap hooks 145 and the silicone check valve 149.

FIG. 11 is a superior perspective view of the universal hub 140 of the catheter 100 of FIG. 1. As can be appreciated in FIG. 11, the universal hub 140 provides support for the manipulation of the catheter tube for insertion into the ureteral orifice and provides stability for use of syringe 106 (shown in FIGS. 4 and 13, among other places). (As shown in FIGS. 2 and 4, the hub 140 is secured by leg strap 148 to the leg of the patient.) The leg strap used to secure the hub 140 to the patient is threaded over the opposed pair of forks 145 in the hub 140 of FIGS. 11 and 12 . . . . On the upper face of hub 140 is provided female fitting 143 configured to receive a syringe for instillation of medicament to the bladder. FIG. 12 is an exploded view of the universal hub in FIG. 11 that sets out a relationship between the universal hub 140 and the hub insert 147 and the combined functionality.

Figure 13:
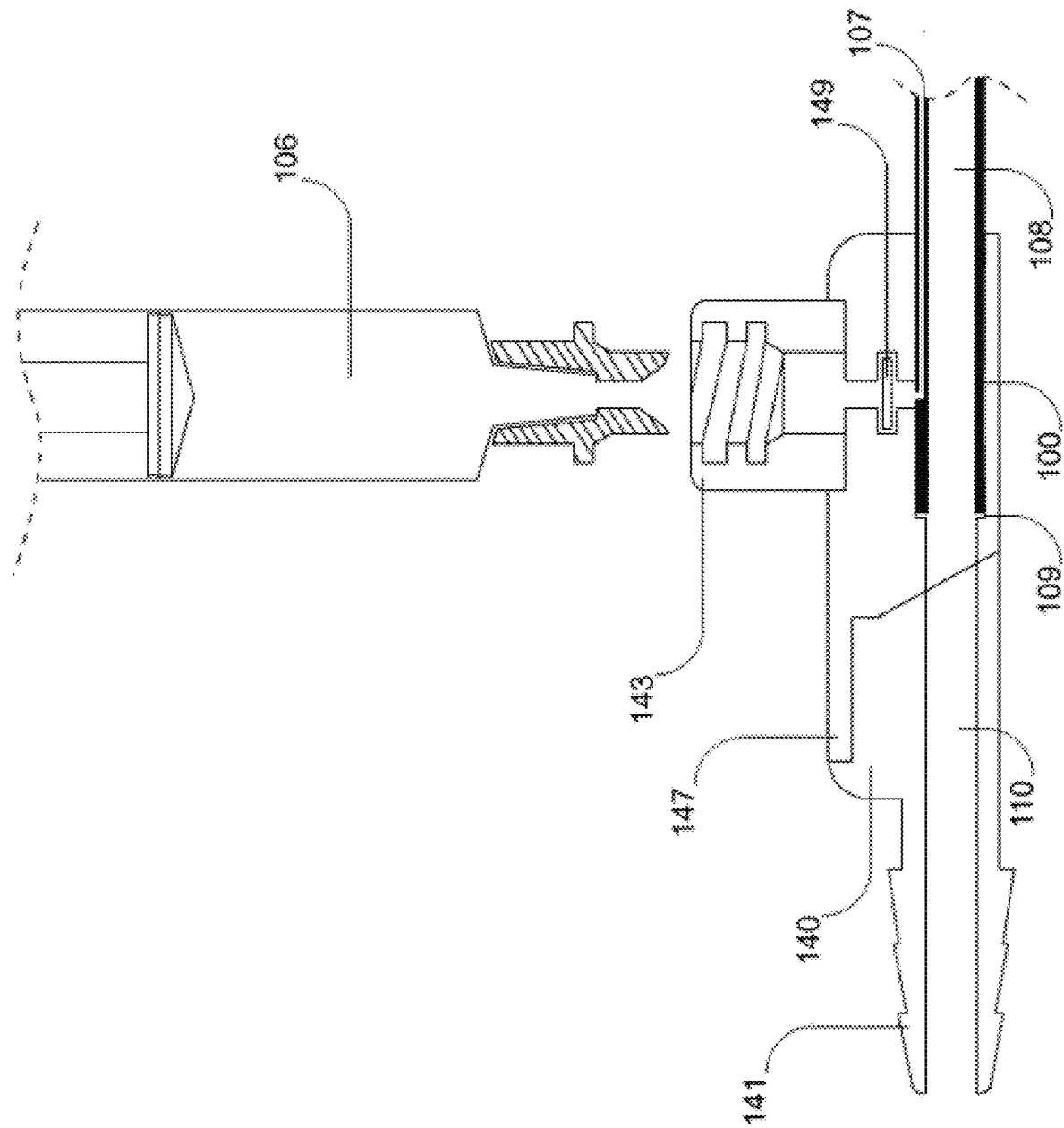
FIG. 13 is a cross-section view of the embodiment of FIG. 1 showing universal hub 140 including the access port connector female and male connector designed to avoid misconnections attached to a Luer syringe with Luer and other connectors.

FIG. 13 is a cross-section view of the universal hub 140 with the hub insert 147 fixed in position by UV cured medical grade adhesive. At its distal end, a urine drainage tube (that is normally attached to the urine bag) is coupled using the integrated male connector 141, that is integrated into the universal hub 140, and which permits the collection of urine. The portal end is inserted into the bladder of the patient, through the urethra with the eyelets in the open position to begin the drainage of urine from the bladder. FIG. 13 also shows the relationship and the integration of the key functionality of the components.

An important benefit of the universal hub 140 is its ability to accommodate different diameter catheters via the hub insert 147. The use of the hub insert 147 reduces tooling costs that would otherwise be required in using different hubs for different catheters 100 of different tubing sizes. The hub insert 147 is inserted into the universal hub 140 of FIG. 13. The distal end of the catheter tubing 100 terminates within the hub insert 147 of FIG. 13. As shown in FIG. 13, within the hub insert 147, the urinary lumen 108 abuts a flange 109 to provide a good fluid connection to the hub insert and a flow path to the male fitting 141 for drainage of urine. Similarly, the instillation lumen 107 is coupled through a hole near the distal end of the catheter external wall to receive medicament from a syringe 106 placed in the female coupling 143 (in FIGS. 11-13). The medicament flows through an integrated silicone check valve 149 (in FIGS. 12 and 13) to prevent backflow of the medicament both during and after instillation.

As shown in FIGS. 11 and 12, the hub insert 147 is configured to fit into a single-sized universal hub base 140, while the dimensions of the hub insert 147 itself can be configured to accommodate any of a range of sizes of catheter tubes and urinary and instillation lumens therein. The unique connector diameter and shape of the female coupling 143 fits the syringe male coupling and engagement lugs 106, to avoid misconnection mistakes, which can otherwise occur in care facilities, hospitals, and especially self-medication procedures.

Figure 14:
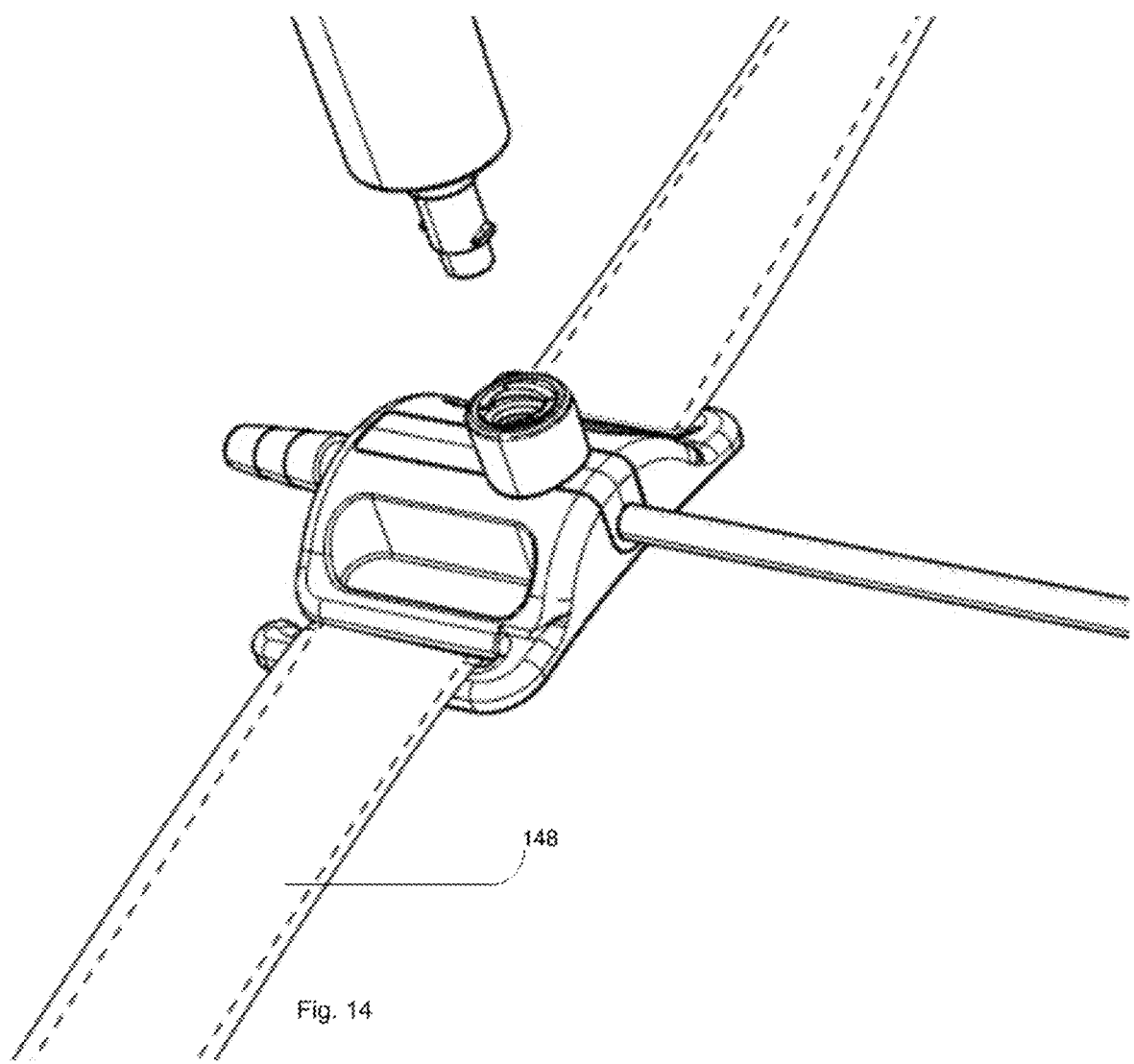
FIG. 14 is a perspective view of the universal hub 140 of FIG. 11 with the leg straps hooks 145 and the leg strap 148 which is the preferred option for the universal hun securement.

FIG. 14 is a perspective view of the universal hub 140 of FIG. 11 with the leg strap hooks 145 of FIG. 11 and the leg strap 148 which is the preferred option for the universal hub securement.

Figure 15:
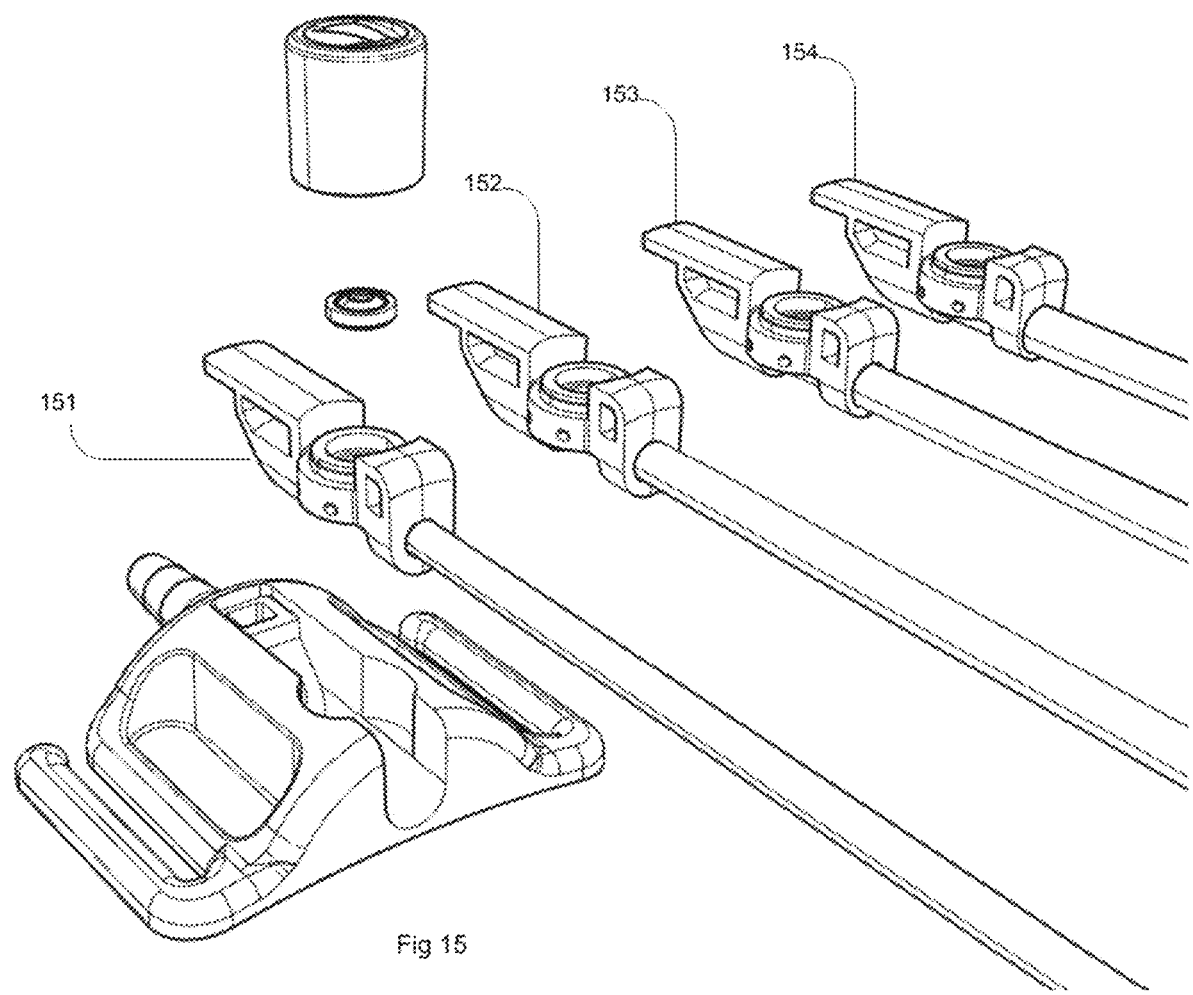

FIG. 15 is a perspective view of the universal hub 140 of FIG. 11 with four instances of the tube 100 of FIG. 11 and its corresponding insert 147 of FIG. 11, wherein each successive instance 151, 152, 153, and 154 has a larger diameter than its predecessor corresponding respectively to 12 Fr., 14 Fr., 16 Fr., and 18 Fr.

What is claimed is:

1. An intravesical intermittent instillation catheter comprising:
   a tube, dimensioned and shaped for partial insertion into a urinary conduit of a patient, the tube containing a urinary lumen and an instillation lumen, the tube having a distal end and a proximal end, wherein the proximal end has a set of drainage eyelets, formed in a wall thereof, that are in communication with the urinary lumen as well as a set of instillation eyelets, formed at a tip of the proximal end, in communication with the instillation lumen;
   a sheath having a distal end and a proximal end, the sheath being slidably mounted to surround the tube and having first and second axial positions in relation to the tube, wherein, in the first position, the drainage eyelets are exposed and, in the second position, the drainage eyelets are covered by the proximal end of the sheath;
   a valve actuator configured at a distal end of the sheath, the actuator including (i) a slider coupled to the sheath and sliding with the sheath and (ii) an anchor coupled to the tube, each of the slider and the anchor being configured to be grasped by a different hand, wherein movement of the slider away from the anchor causes the sheath to move to the second position so as to cover the eyelets and prevent further flow of urine therethrough; and a hub mechanically coupled to a distal end of the tube and including an installation connector coupled to the instillation lumen and a drainage connector coupled to the urinary lumen, wherein the drainage connector is configured to be connected to tubing configured to be coupled to a urinary collection bag and the instillation connector is configured to be coupled to a syringe filled with a medicament for instillation into the bladder;

so that, when the sheath is in the first position, drainage of urine can proceed through a path including the drainage eyelets, the urinary lumen, the drainage connector, and the urinary collection bag and, when the sheath is in the second position, instillation of the medicament can thereafter proceed from the syringe, through the installation connector, the instillation lumen, and the installation eyelets and into the bladder.

2. An intravesical intermittent instillation catheter according to claim 1, wherein the installation connector is configured to receive a custom-shaped medicament-containing syringe that is incompatible with a conventional Luer syringe, so as to reduce a risk of inadvertent use of an improper medicament or dosage.

3. An intravesical intermittent instillation catheter according to claim 1, wherein the valve actuator further includes a one-way latch configured, when the slider has been advanced in the proximal direction, to occupy space between the slider and the anchor so as to prevent return motion of the slider to the distal position for reuse of the catheter.

4. An intravesical intermittent instillation catheter according to claim 1, wherein the hub includes a hub insert, to which the tube is attached and configured so that the urinary lumen therein has a flow path to the drainage connector for drainage of urine therethrough and the instillation lumen has a flow path through a hole near the distal end of an external wall of the catheter to receive medicament from a syringe placed in the installation connector, wherein the hub insert is customized to one size of a specific set of sizes associated with the tube, the installation lumen, and the urinary lumen, so that the hub can accommodate a variety of sizes associated with the tube, the installation lumen, and the urinary lumen.

5. An intravesical intermittent instillation catheter according to claim 1, wherein the hub insert includes an integrated check valve, in the flow path between the installation connector and the hole near the distal end of the external wall of the catheter, to prevent backflow of the medicament during instillation of the medicament.

6. An intravesical intermittent instillation catheter according to claim 1, wherein at its proximal end the sheath has an edge that is generally bevelled to minimize trauma to surrounding tissue when the sheath is moved to the second position.

7. An intravesical intermittent instillation catheter according to claim 1, wherein the sheath, over a majority of its length, has an internal diameter that exceeds an external diameter of the catheter, by an amount sufficient to facilitate ready sliding of the sheath over the catheter, but wherein the internal diameter of the sheath is tapered to a tight tolerance near the proximal end of the sheath, with the tolerance still permitting sliding of the sheath while also preventing flow of fluid between the sheath and the exterior of the catheter.

* * * * *